(12) United States Patent
Shafikhani (10) Patent No.: US 9,981,011 B2
(45) Date of Patent: May 29, 2018

(54) METHODS OF PROMOTION OF HEALING OF DIABETIC WOUNDS

(71) Applicant: Rush University Medical Center, Chicago, IL (US)

(72) Inventor: Sasha Shafikhani, Elmwood Park, IL (US)

(73) Assignee: Rush University Medical Center, Chicago, IL (US)

( * ) Notice: Subject to any disclaimer, the term of this patent is extended or adjusted under 35 U.S.C. 154(b) by 0 days. days.

(21) Appl. No.: 15/123,872

(22) PCT Filed: Mar. 9, 2015

(86) PCT No.: PCT/US2015/019385
§ 371 (c)(1),
(2) Date: Sep. 6, 2016

(87) PCT Pub. No.: WO2015/138288
PCT Pub. Date: Sep. 17, 2015

(65) Prior Publication Data
US 2017/0014484 A1 Jan. 19, 2017

Related U.S. Application Data

(60) Provisional application No. 61/950,740, filed on Mar. 10, 2014.

(51) Int. Cl.
| | | |
|---|---|---|
| *A61K 38/00* | (2006.01) | |
| *A61K 38/16* | (2006.01) | |
| *A61K 38/19* | (2006.01) | |
| *A61K 38/20* | (2006.01) | |
| *A61K 9/00* | (2006.01) | |
| *A61K 31/23* | (2006.01) | |
| *A61K 45/06* | (2006.01) | |

(52) U.S. Cl.
CPC .......... *A61K 38/195* (2013.01); *A61K 9/0014* (2013.01); *A61K 31/23* (2013.01); *A61K 38/193* (2013.01); *A61K 38/2006* (2013.01); *A61K 45/06* (2013.01)

(58) Field of Classification Search
None
See application file for complete search history.

(56) References Cited

U.S. PATENT DOCUMENTS 8,835,170 B2 * 9/2014 Katz ................ A61K 35/28
424/93.3
2010/0111897 A1 5/2010 Katz et al.
2012/0329729 A1 * 12/2012 Rodgers ............... A61K 38/085
514/21.7

OTHER PUBLICATIONS

Green et al. 2012. J. Leukoc Biol. 92:633-39.*
De Sonnaville et al.; "The prevalence and determinants of foot ulceration in type II diabetic patients in a primary healthcare setting"; retrieved from the Internet on Apr. 30, 2015 at http://www.ncbi.nim.nih.gov/pubmed/9179471; Diabetes Res. Clin. Pract., vol. 35, Issues 2-3; pp. 149-156; Mar. 1997; Abstract.
Low et al.; "Wound Healing in MIP-1 alpha-/- and MCP-1-/- Mice"; retrieved from the Internet on Apr. 30, 2015 at http://www.ncbi.nim.nih.gov/pmc/articles/PMC1850564/pdf/2752.pdf.; American Journal of Pathology, vol. 159, Issue 2; pp. 457-463; Aug. 2001.
Wood et al.; "Pro-Inflammatory Chemokine CCL2 (MCP-1) Promotes Healing in Diabetic Wounds by Restoring the Macrophage Response"; retrieved from the Internet on Apr. 30, 2015 at http://www.cnbi.nim.nih.gov/pmc/articles/PMC3950222/pdf/pone.0091574.pdf; Plos One, vol. 9, Issue 3; e91574; 8 pages; Mar. 2014.
International Search Report dated Jun. 8, 2015 for International Application No. PCT/US2015/019385.
Written Opinion of the International Searching Authority dated Jun. 8, 2015 for International Application No. PCT/US2015/019385.

* cited by examiner

*Primary Examiner* — Shulamith H Shafer
(74) *Attorney, Agent, or Firm* — Brinks Gilson & Lione (57) ABSTRACT

A method of treating a wound in a diabetic patient is provided. The method includes administering a therapeutically effective amount of Chemokine (C-C motif) ligand 2 (CCL2) to a wound site. In another aspect, a method of treating a wound in a diabetic patient is provided. The method includes assaying a level of CCL2 in the diabetic patient relative to a level of CCL2 in a normal subject and administering a therapeutically effective amount of CCL2 to the diabetic patient.

16 Claims, 12 Drawing Sheets

METHODS OF PROMOTION OF HEALING OF DIABETIC WOUNDS

RELATED APPLICATIONS

This application claims the benefit under 35 U.S.C. § 371 of International Application No. PCT/US2015/019385, filed Mar. 9, 2015, which claims the benefit of U.S. Provisional Application No. 61/950,740, filed Mar. 10, 2014, which are incorporated by reference herein in their entirety.

This application claims the benefit of U.S. Provisional Application No. 61/950,740, filed Mar. 10, 2014, which is incorporated by reference herein in its entirety.

BACKGROUND

The present invention relates to methods of treatments of disease. More particularly, the invention relates to a method of treating a wound in a diabetic patient by administering a dose of a cytokine.

Impaired healing seen in diabetic wounds has been hypothesized to be derived from a state of persistent hyper-inflammation characterized by harmful increases in inflammatory leukocytes including macrophages at the wound site. However, studies of such phenomena have focused on wounds at later time points (that is, about ten days old or older), and little attention has been given to the dynamics of macrophage responses in diabetic wounds early after injury.

Given the importance of macrophages for the process of healing, it is desirable to modulate the dynamics of macrophage response during early and late phases of healing in diabetic wounds in order to promote better outcomes for patients.

SUMMARY

According to a first aspect of the present invention, a method of treating a wound in a diabetic patient is provided. The method includes administering a therapeutically effective amount of Chemokine (C-C motif) ligand 2 (CCL2) to a wound site.

In another aspect, a method of treating a wound in a diabetic patient is provided. The method includes assaying a level of CCL2 in the diabetic patient relative to a level of CCL2 in a normal subject and administering a therapeutically effective amount of CCL2 to the diabetic patient.

Further aspects, features, and advantages of the invention will become apparent from consideration of the following description and the appended claims when taken in connection with the accompanying figures.

BRIEF DESCRIPTION OF THE DRAWINGS

Embodiments of the present invention are described below, by way of example only with reference to the accompanying drawings in which:

FIG. 4B is a bar graph quantifying the fold expression of CCL2 at wound sites in a wild-type and in a diabetic mouse;

DETAILED DESCRIPTION

It is to be understood that the figures are schematic and representative of the experiments conducted.

The terms "substantially" or "about" used herein with reference to a quantity includes variations in the recited quantity that are equivalent to the quantity recited, such as an amount that is equivalent to the quantity recited for an intended purpose or function.

Statistical analyses listed throughout this specification are performed by one-way analysis of variance, Bartlett's test for equal variances, or Student t-test using statistical analysis software. Data are presented as mean± standard error of the mean. P-values less than or equal to 0.05 were taken as significant.

Studies of wound healing in diabetic patients have typically focused on wounds at about ten days after wounding or older and have typically drawn the conclusion that impaired healing of these wounds derives from a state of persistent hyper-inflammation characterized by harmful increases in inflammatory leukocytes such as macrophages. The dynamics of macrophage responses in diabetic wounds early after injury, however, run contrary to the prevailing hypothesis, the diabetic wound exhibits a significant delay in macrophage infiltration.

The delay in the macrophage response in diabetic wounds can result from a reduction in the level of chemokine (C-C motif) ligand 2 (CCL2) expression. In such cases even one-time treatment with CCL2 can significantly stimulate healing in diabetic wounds by restoring the macrophage response. Thus, rather than a hyper-inflammatory state; the early diabetic wound exhibits a paradoxical and damaging decrease in essential macrophage response. The restoration of the proper kinetics of macrophage response may be able to jumpstart subsequent healing stages.

In normal settings, acute inflammatory response occurs early to fight off invading pathogens and to jumpstart healing through the production of chemokines, cytokines, and growth factors. It also resolves quickly so as not to perturb subsequent stages of repair. In pathological conditions such as diabetic ulcers, inflammation can become locked in a non-resolving mode and can be a major culprit that contributes to impaired healing in these settings.

Macrophages destroy invading pathogens, clear cellular debris, and express a multitude of cytokines, chemokines, and growth factors, which mediate subsequent healing stages. A preponderance of evidence points to a central role for macrophages in mediating effective repair in normal settings.

In the diabetic chronic wound setting, however, prior studies suggest that the impaired healing can derive from a state of persistent hyper-inflammation characterized by harmful increases in inflammatory leukocytes including macrophages. As stated before, such studies have tended to focus on older (10 or more days old) wounds. Studies of newer wounds, on the other hand, suggest that insufficient macrophage response and/or activity early after injury may also contribute to healing impairment in diabetic wounds. It is known that monocyte and macrophage recruitment into the peritoneal cavity in response to thioglycolate can be significantly diminished in diabetic mice compared to a healthy control group. The study that determined this demonstrates that addition of interleukin-1-beta-treated activated macrophages to diabetic wounds enhanced healing.

The following exemplary experimental results suggest that rather than a hyper-inflammatory state; the early diabetic wound exhibits a damaging delay in essential macrophage response. The delay in macrophage response can be due to insufficient chemokine expression. One-time treatment with the pro-inflammatory chemokine CCL2 (also known as MCP-1) can activate the macrophage response and stimulate healing, suggesting that CCL2 chemokine-based therapy may be an attractive strategy to promote healing in diabetic wound. CCL2 may be administered to patients that have Type I or Type II diabetes.

Figures 1A, 1B:
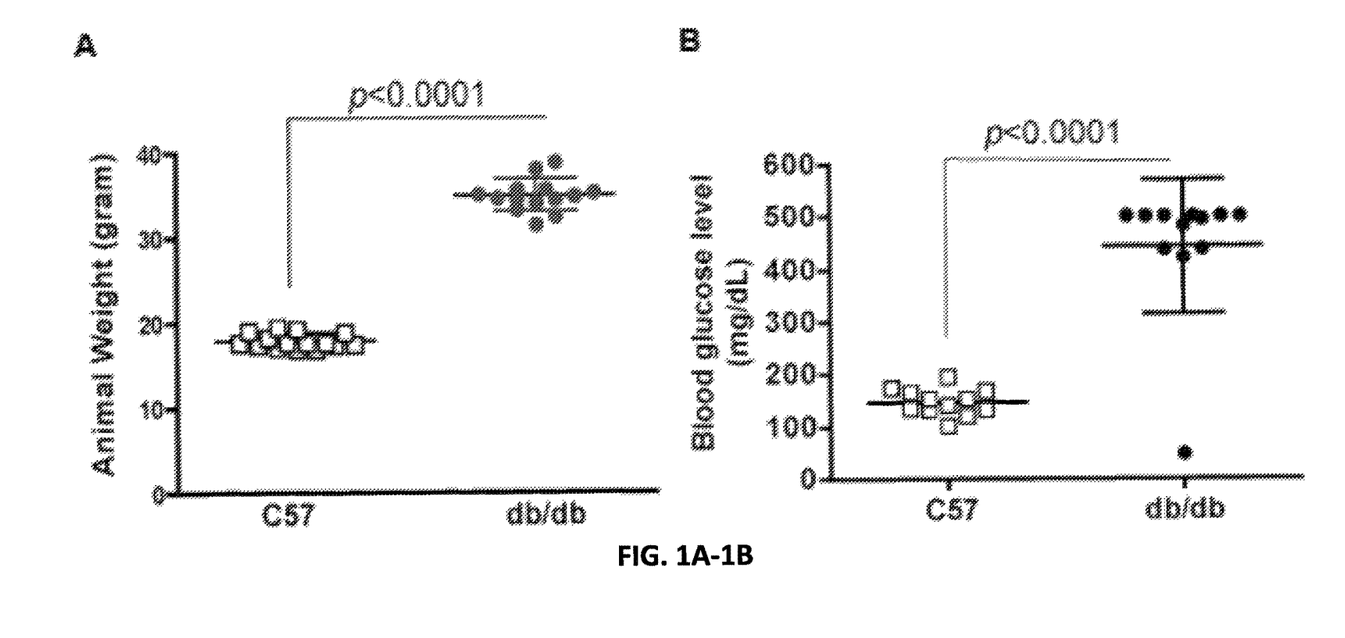
FIG. 1A-1B are graphical representations of weights and blood glucose levels from wild-type and diabetic mice.

Turning now to FIG. 1, a mouse model for type II diabetes, C57BLKS-m lepr$^{db}$ (hereafter db/db) and their wild-type littermates C57BL/6 (hereafter C57) contrast the dynamics of macrophage response in diabetic and normal wounds respectively. In db/db mice, the gene encoding the leptin receptor (ObR) is mutated. Similar mutations in leptin and the leptin receptor also occur in humans and have been linked to type II diabetes.

Figures 1C, 1D:
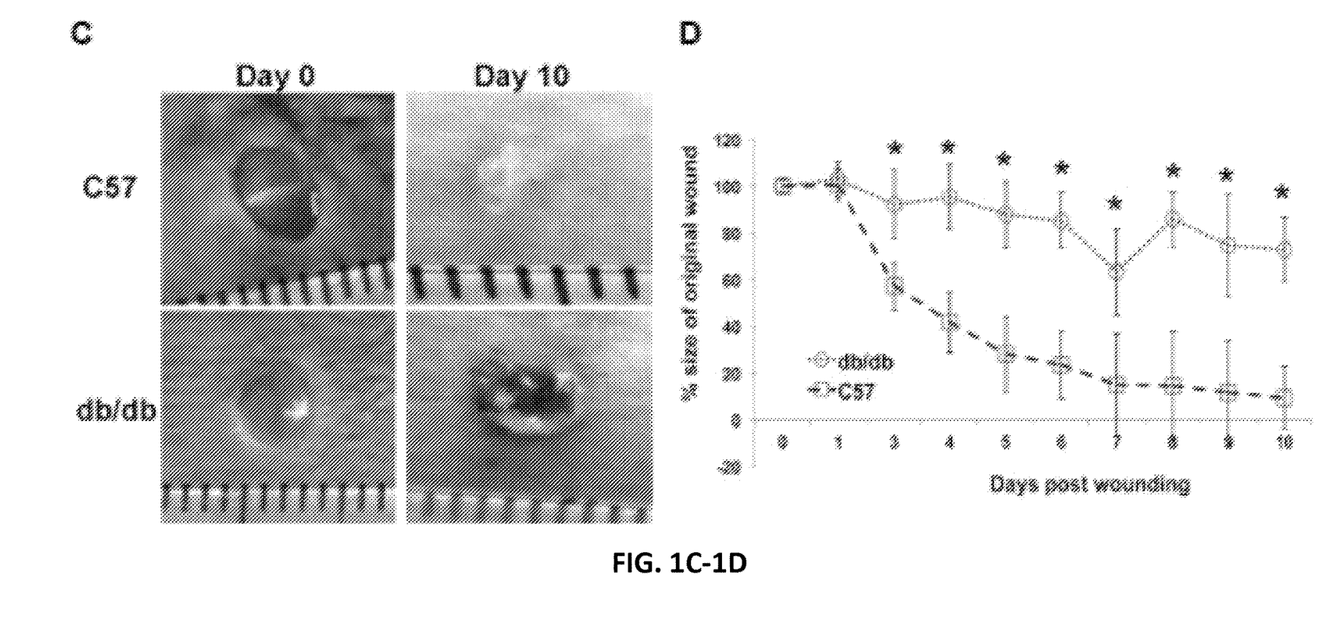
FIG. 1C are photographs of wounds in wild-type and diabetic mice 0 days and 10 days after wounding.
FIG. 1D is a graphical representation of the size of wounds sustained by wild-type and diabetic mice over the course of 10 days post wounding as a percentage of the original size of the wound.

As shown in FIG. 1C, full-thickness incisional wounds are generated on the back skin of db/db diabetic and C57 wild-type mice. One way of creating such wounds is by using a sterile biopsy punch, for instance 3 millimeters or 5 millimeters in diameter. The punch is used to punch through the full thickness of the back skin below the shoulder blades in normal (C57Bl/6) mice and their diabetic littermates, C57BLKS-m lepr$^{db}$ (db/db). For wound healing assessment, transparency paper is used to trace the wound edges. The wound areas can be subsequently calculated using imaging software, such as NIH ImageJ software].

Wound healing can be assessed at 24 hr interval by digital photography and expressed as percent wound remaining, calculated as the percentage of original wound area {(open wound area/initial wound area)×100}. For immunohistological (IHC) studies, wound tissues can be harvested, snap-frozen and embedded in a resin such as TISSUE-TEK O.C.T. from Sakura. The tissues can alternatively be fixed in 10% formalin, transversely cut into for example about 7-μm-thick sections from the middle part of the wounds, and stained with hematoxylin and eosin (H&E) or CD68 antibody which primarily stains macrophages.

Consistent with previous reports, db/db mice developed obesity (FIG. 1A) and severe diabetes with marked hyperglycemia (FIG. 1B), and exhibited impaired wound healing resembling human adult-onset diabetes mellitus (FIG. 1D).

Figure 2A:
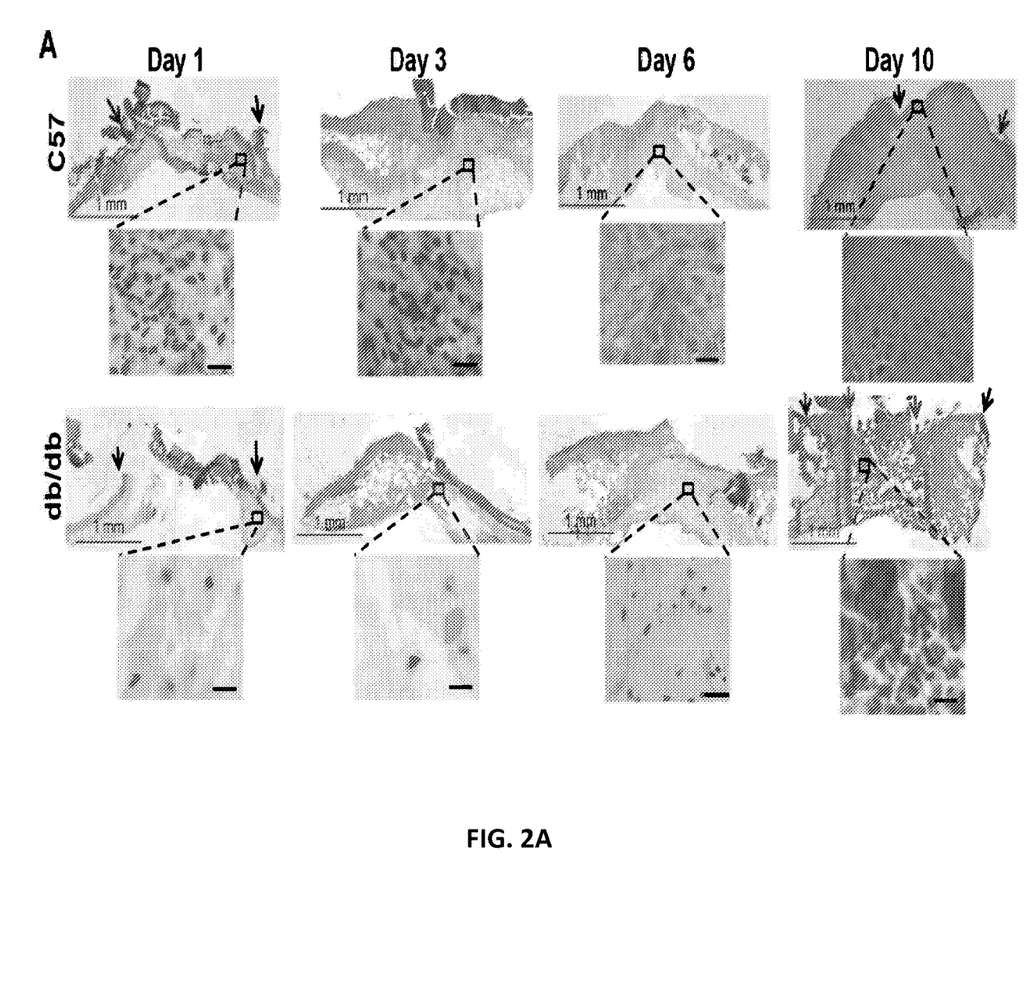
FIG. 2A-2B are photographs of histological sections taken from skin tissues of a wounded mouse representing a time course of the progression of wound healing in diabetic versus control skin tissues.

Turning now to FIG. 2, histological analyses using hematoxylin and eosin (hereafter H&E) tissue staining, which can be used to evaluate the inflammatory response in various normal and pathologic conditions including wounds, are shown. The tissues illustrated are wound tissues from C57 and db/db mice and the samples represent days 1, 3, 6, and 10 after wounding. The results indicate that the inflammatory response is delayed in db/db wounds. Normal wounds from C57 mice exhibit infiltration of inflammatory cells on days 1 and 3 but inflammation begins to subside by day 6 and is mostly resolved by day 10 (FIG. 2A). Day 10 normal wounds are fully re-epithelialized, and exhibit contraction, epidermal thickening, and substantial granulation.

In contrast, inflammation is minimal on days 1, 3, and 6 in db/db wounds but by day 10 post injury, diabetic wounds contain substantially more inflammatory leukocytes than day 10 normal wounds (FIG. 2A).

Figure 2B:
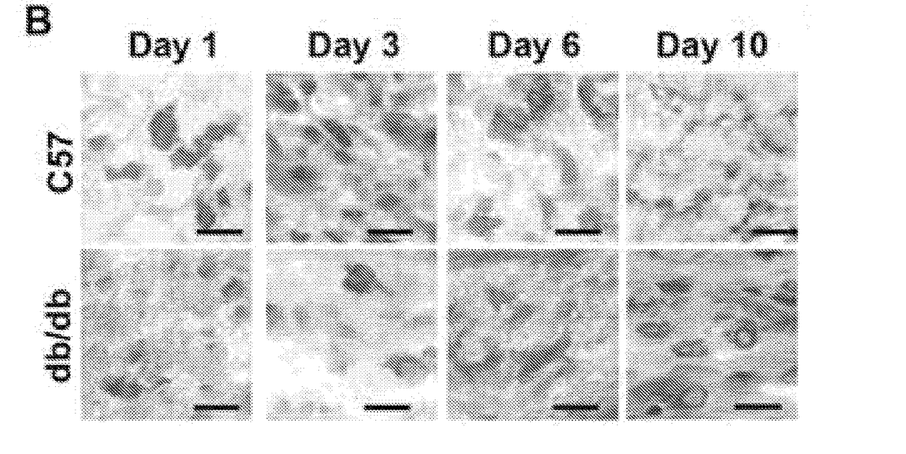
Figure 2C:
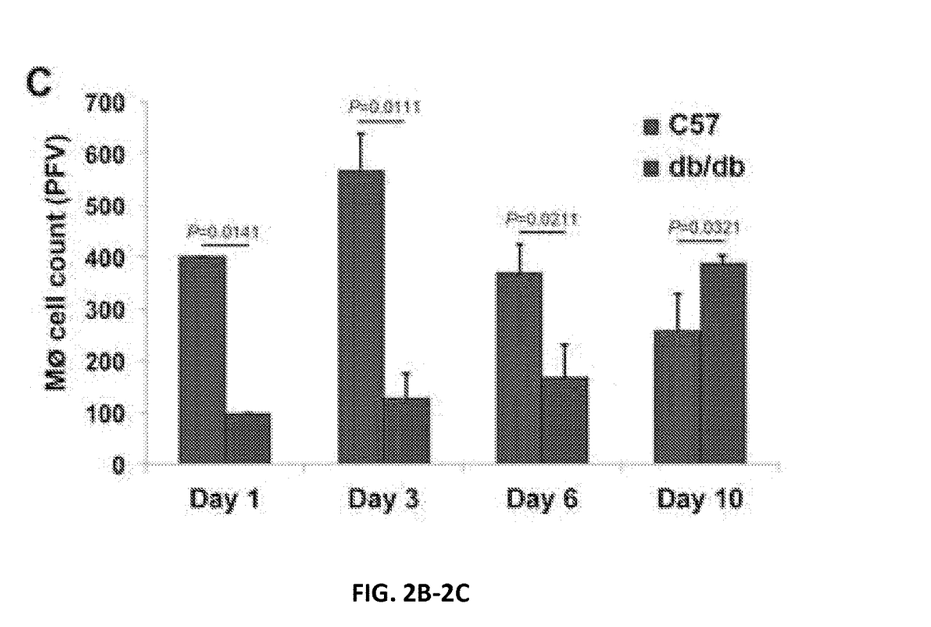
FIG. 2C is a bar graph of macrophage counts at wound sites in the skin tissues of FIG. 2A-2B at various time points.

Further, to assess the dynamics of macrophage response during wound healing, C57 and db/db wound tissues from days 1, 3, 6, and 10 can be stained with antiCD68 antibody, which primarily stains macrophages. Consistent with H&E staining results (FIG. 2A), diminution in the macrophage signal can be observed early after injury in days 1, 3, and 6 of db/db wounds but recovery occurs by day 10 (FIGS. 2B and 2C, p≤0.0321, n=18).

Figure 3A:
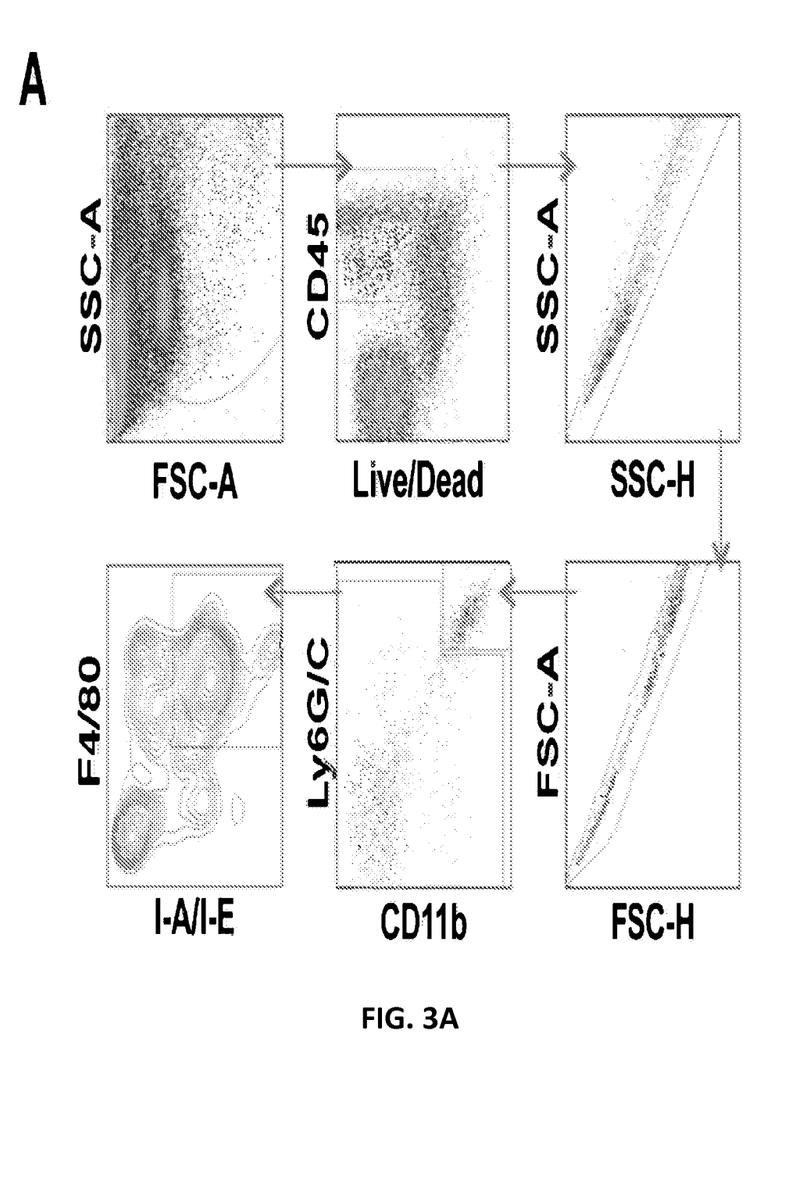
FIG. 3A-3B are representations of data collected during flow cytometry experiments that illustrate impaired macrophage response at wound sites of diabetic patients.
Figures 3B, 3C:
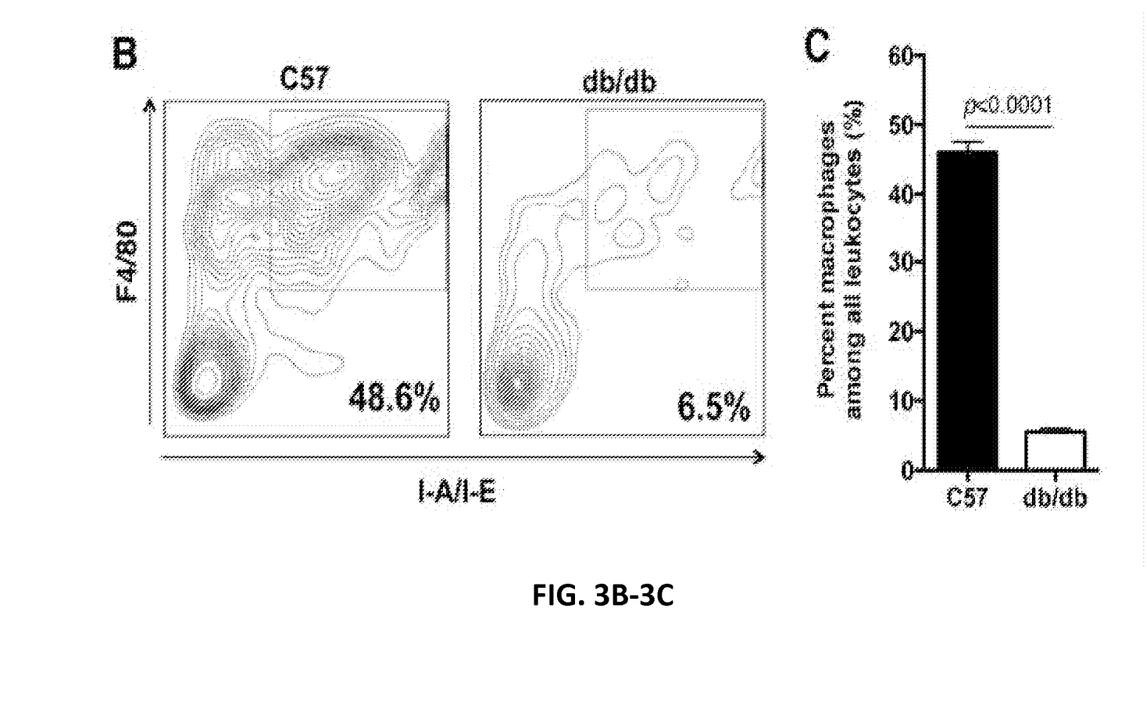
FIG. 3C is a bar graph quantifying the number of macrophages among collected leukocytes at a wound site in a wild-type and diabetic mouse model.

Turning to FIG. 3, CD68 antibody also reacts with myeloid precursors, peripheral blood granulocytes, and plasmacytoid dendritic cells so In order to specifically observe macrophages, total cells extracted from equal amounts of C57 and db/db day 1 tissues (approximately 1 millimeter from the wound edge) can be analyzed for macrophage cell content (defined as CD45+ F4/80+ I-A/I-E+) by flow cytometry.

To conduct flow cytometry analysis, C57 and db/db skin tissues can be obtained on day 1 via 5 mm punch biopsies, weighed, and placed in solution. Subcutaneous fat is removed using, for example, a scalpel, and scissors can be used to cut the tissue into small (<2 mm) pieces. The tissue is enzymatically dissociated in DNAse I (40 μg/ml) and Colagenase D (1 mg/ml HBSS) at 37° C. for 30 minutes. Cold phosphate buffered saline (PBS) is used to stop the dissociation process. The tissue can then mechanically dissociated and passed through 70 μm nylon screens into 50 ml conical tubes. Cells can then be washed twice with PBS.

Resultant single-cell suspensions are stained using fluorescently labeled antibodies against cell surface markers, according to any standard protocol known in the art. Flow cytometry is then performed in the usual way. One gating strategy employed in the trial of FIG. 3 identifies live leukocytes by using a lymphocyte (FSC-A vs SSCA) gate followed by a CD45 versus Live/Dead gate (where leukocytes are CD45+ and live cells are negative for Live/Dead). Doublets are excluded using SSC-A vs. SSC-H and FSC-A vs. FSC-H gating. Lastly, neutrophils are identified as Ly6C/GhiCD11bhi cells and macrophages were identified as non-neutrophil F4/80+1-A/I-E+ cells.

The data demonstrate an over 7-fold reduction in the percentage of macrophages among all leukocytes in day 1 diabetic wounds, indicating that the macrophage response, among all other leukocytes that constitute the inflammatory response, is particularly impaired in diabetic wounds early after injury (FIG. 3, p<0.0001, n=5).

Figures 4A, 4C:
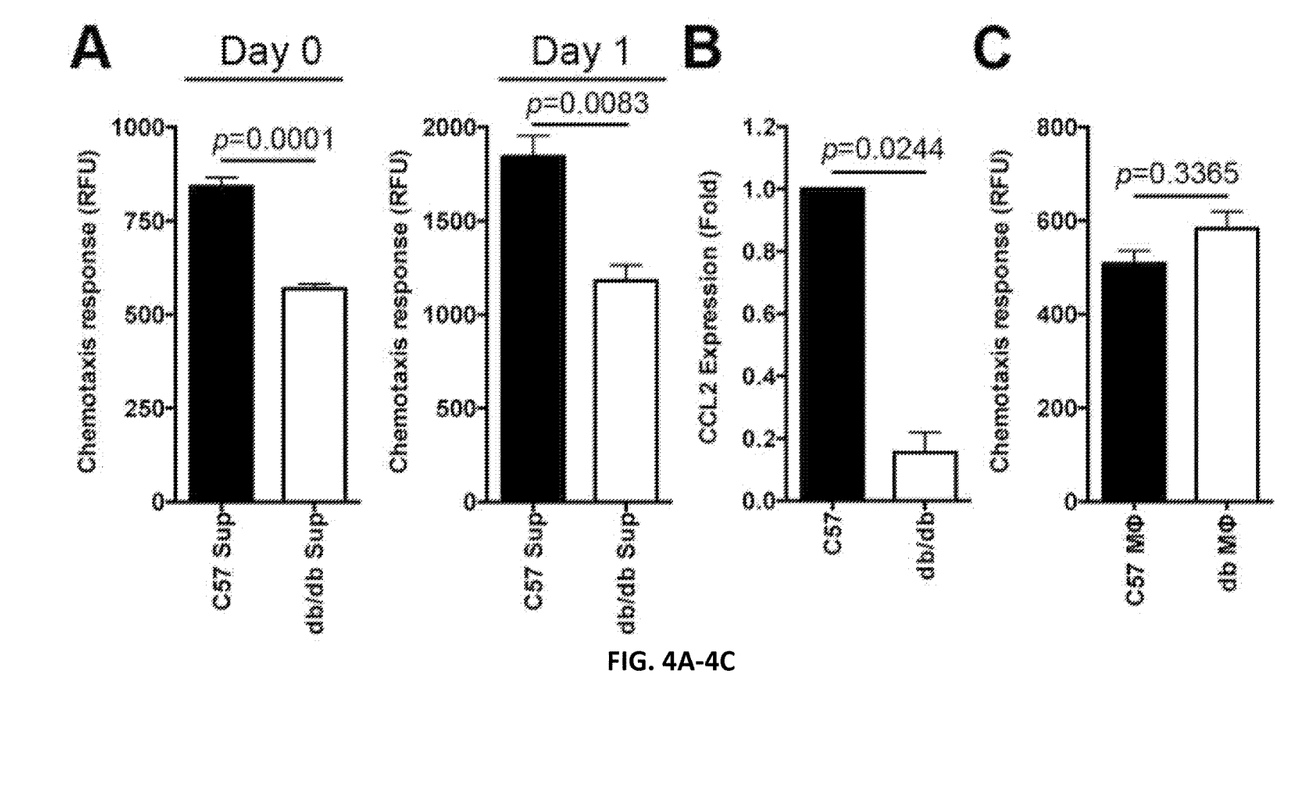
FIGS. 4A and 4C are bar graphs illustrating chemotactic responses of macrophages to secreted or purified cytokines.

Turning now to FIG. 4, chemokine expression can account for delayed macrophage response in db/db wounds early after injury as indicated by a functional assay. To evaluate the capacity of normal and diabetic skin tissues to express chemoattractants for macrophages, equal amounts of normal and diabetic skin tissues (~1 mm from the edge) are harvested on day 0 (right after wounding) and on day 1 post wounding. These tissue explants are cultured and allowed to secrete chemokines into culture media. The supernatants from these tissue explant cultures are evaluated for their chemokine contents by assessing their ability to chemoattract normal macrophages from C57 mice. The results indicate that supernatants from day 0 and day 1 of diabetic skin tissues contain significantly reduced chemoattractants for macrophages. (FIG. 4A, p<0.0001 for day 0 and p<0.0083 for day 1, n=18, 6 mice per group, each done in triplicates).

To assess the ability of normal and diabetic wound tissues to express chemoattractants, equal amounts of day 1 wound tissues from C57 and db/db are harvested and incubated in 5 ml of keratinocyte serum-free defined media for 4 days to allow expression and secretion of chemokines into the culture. The chemokine activities contained within the aforementioned culture supernatants (Sup) are then tested for their ability to attract normal or diabetic macrophages in a chemotaxis assay.

To isolate murine macrophages. Briefly, bone marrow from the femurs of C57 or db/db mice are grown on low-attachment plates for 7 days in complete Roswel Park Memorial Institute (RPMI) medium with about 20 ng/ul Macrophage-Colony Stimulating Factor (M-CSF). Macrophages are labeled with calcein AM and a chemotaxis assays using wound cultured media as the chemoattractant can be performed for instance in a 96-well CHEMOTX plate from NeuroProbe for 1 hour at 37 degrees Celsius. Fluorescence of transmigrated macrophages can be determined by quantifying fluorescence on a plate reader.

CCL2 is a potent chemoattractant, which is expressed early after injury in wounds and is essential for monocyte/macrophage response and proper healing. CCL2-l-knockout animals exhibit significant wound healing impairment, indicating that CCL2 plays an important and non-redundant role in wound healing. As indicated in FIG. 4B, CCL2 expression, as assessed by reverse transcription and polymerase chain reaction (RT-PCR), significantly diminished in day 1 db/db wounds (p=0.0244, n=3 mice/group).

To purify RNA for the RT-PCR protocol, skin tissues can placed into a Lysing Matrix D tube from MP Biomedicals along with 1 milliliter of TRIZOL. Tissue can be disrupted using a homogenizer, for instance for 10 cycles at 6.0 m/s for 40 seconds. The RNA can be column purified. cDNA is then generated from the purified RNA using any acceptable kit or method, which are known in the art. RT-PCR is performed on any acceptable cycling system with one of a number of protocols and reagents as selected by the user. The data are preferably analyzed using the 2-$\alpha\alpha$Ct method and are presented as ratio of transcripts for gene of interest normalized to GAPDH or tissue weight, although normalization against another housekeeping gene is also acceptable.

To determine whether diabetic macrophages could also be impaired in their ability to respond to chemokines, diabetic and normal macrophages can be tested for their ability to chemotax toward CCL2. After analysis, there are no significant differences in chemotactic responses between normal and diabetic macrophages toward CCL2 (FIG. 4C, p=0.3365). Collectively, data indicated that reduction in CCL2 expression may significantly contribute to impaired macrophage response in diabetic wounds early after injury.

Figures 5A, 5B:
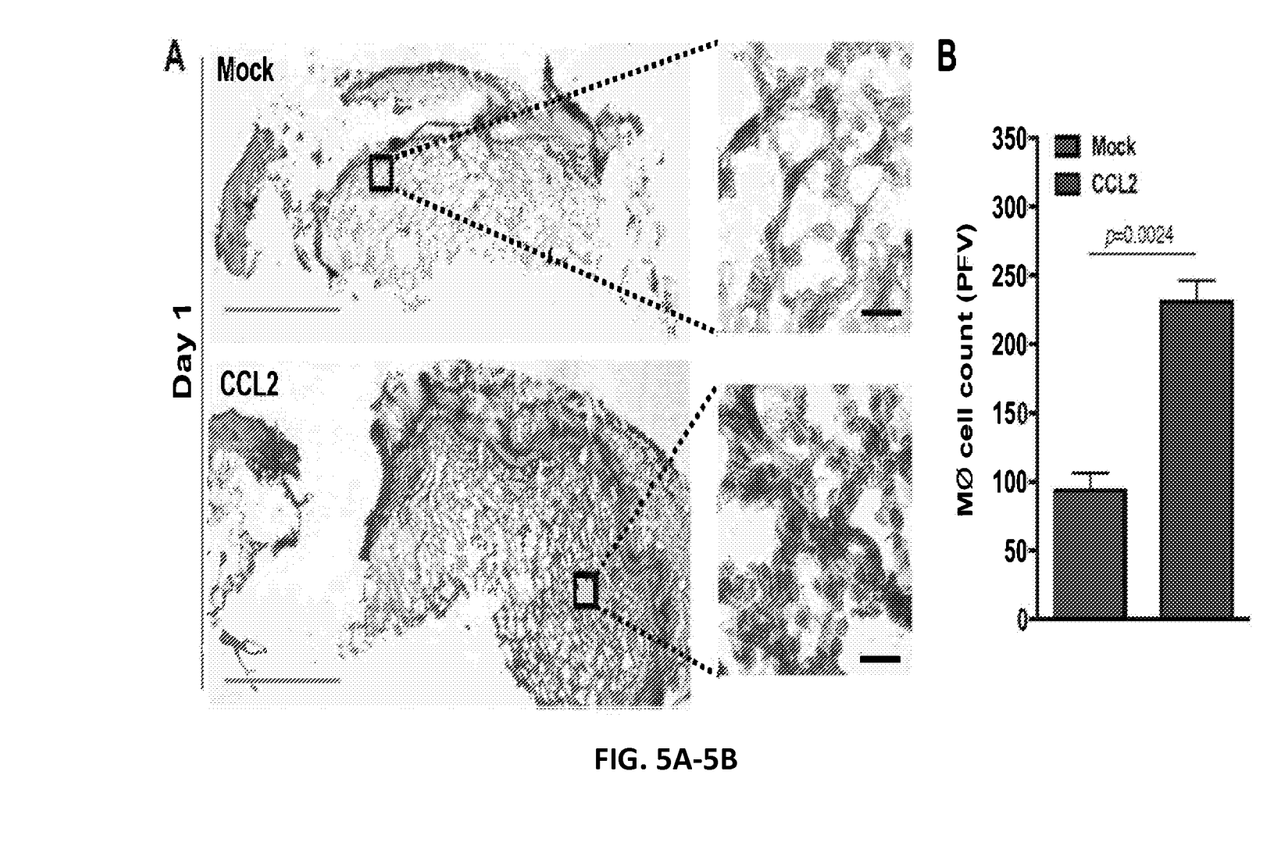
FIGS. 5A and 5C are photographs of histologic sections of diabetic wounds that have been treated with phosphate buffer with or without the cytokine CCL2 and quantitation thereof.
FIGS. 5B and 5D are bar graphs quantifying the macrophage count at wound sites in diabetic mice after mock treatment or treatment with CCL2.

FIG. 5 further confirms that insufficient CCL2 chemokine expression is responsible for delayed macrophage response in diabetic wounds. To restore macrophage influx in diabetic wounds by augmenting wounds with CCL2. db/db wounds are treated once at the time of injury with about 30 ng/wound or most preferably about 60 ng/wound CCL2. CCL2 treatment at about 60 ng/wound significantly enhances macrophage infiltration in day 1 diabetic wounds (FIGS. 5A and 5B, p=0.0024, n=18).

Figures 5C, 5D:
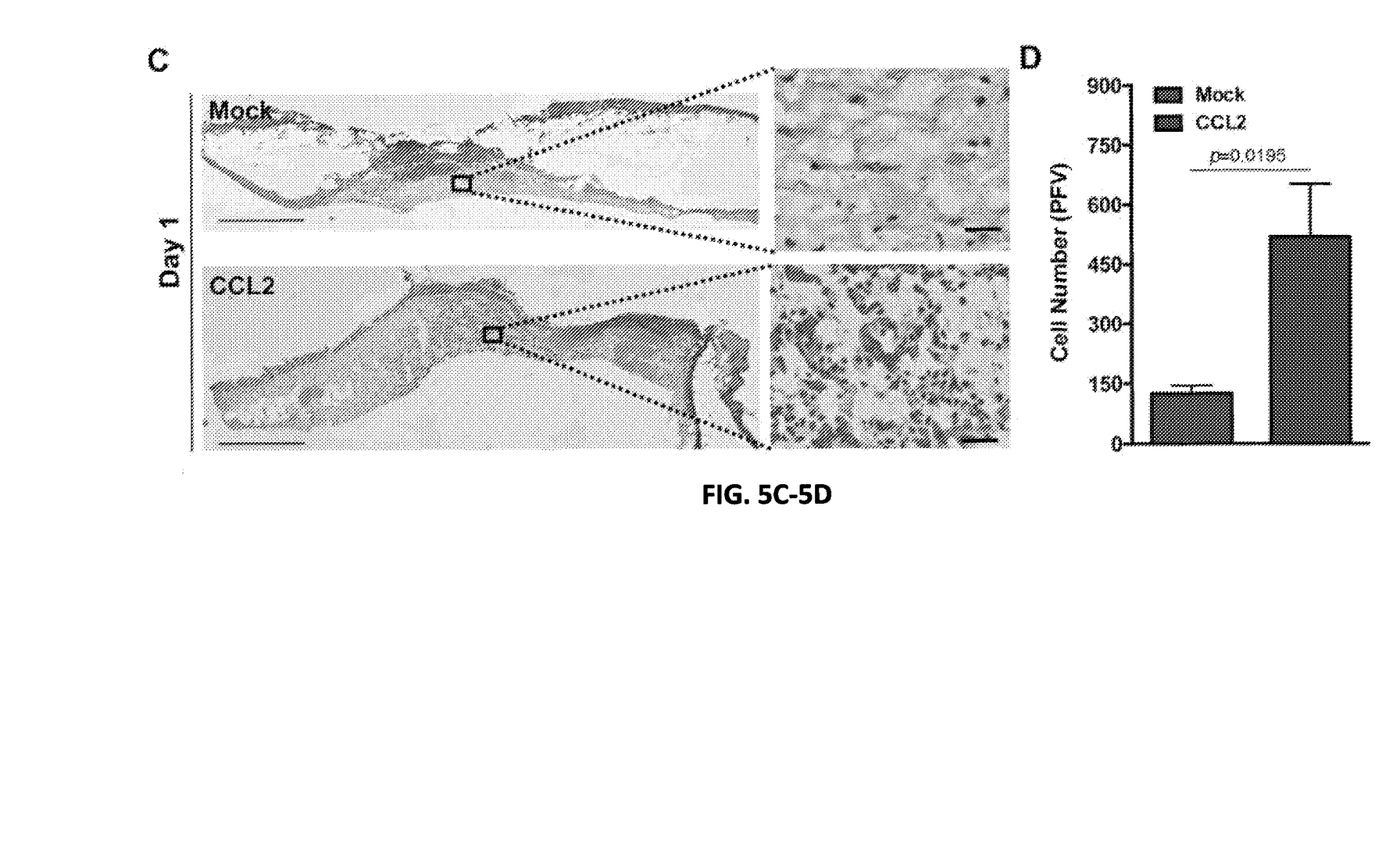

Restoration of the macrophage response by CCL2 treatment is further corroborated by H&E histological analyses, which demonstrate substantial increases in leukocyte infiltration into the CCL2-treated diabetic wounds compared to mock-treated diabetic wounds (FIGS. 5C and 5D, p=0.0195, n=6).

Figures 6A, 6B:
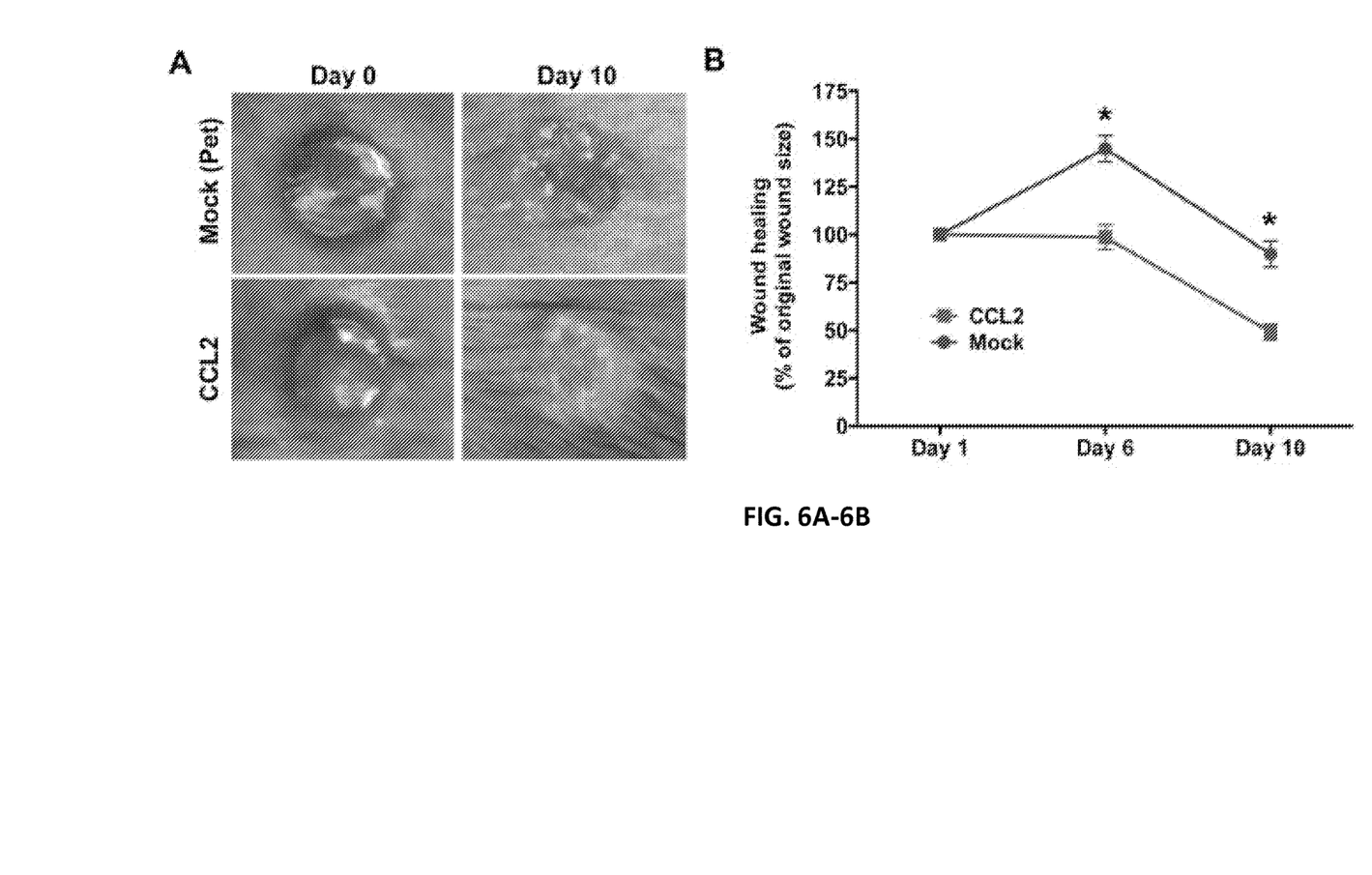
FIG. 6A shows photographs of wounds of a diabetic mouse at 0 days and 10 days after wounding and mock treatment or CCL2 treatment.
FIG. 6B is a graph quantifying results of an experiment similar to that shown in FIG. 6A.
Figures 6C, 6D:
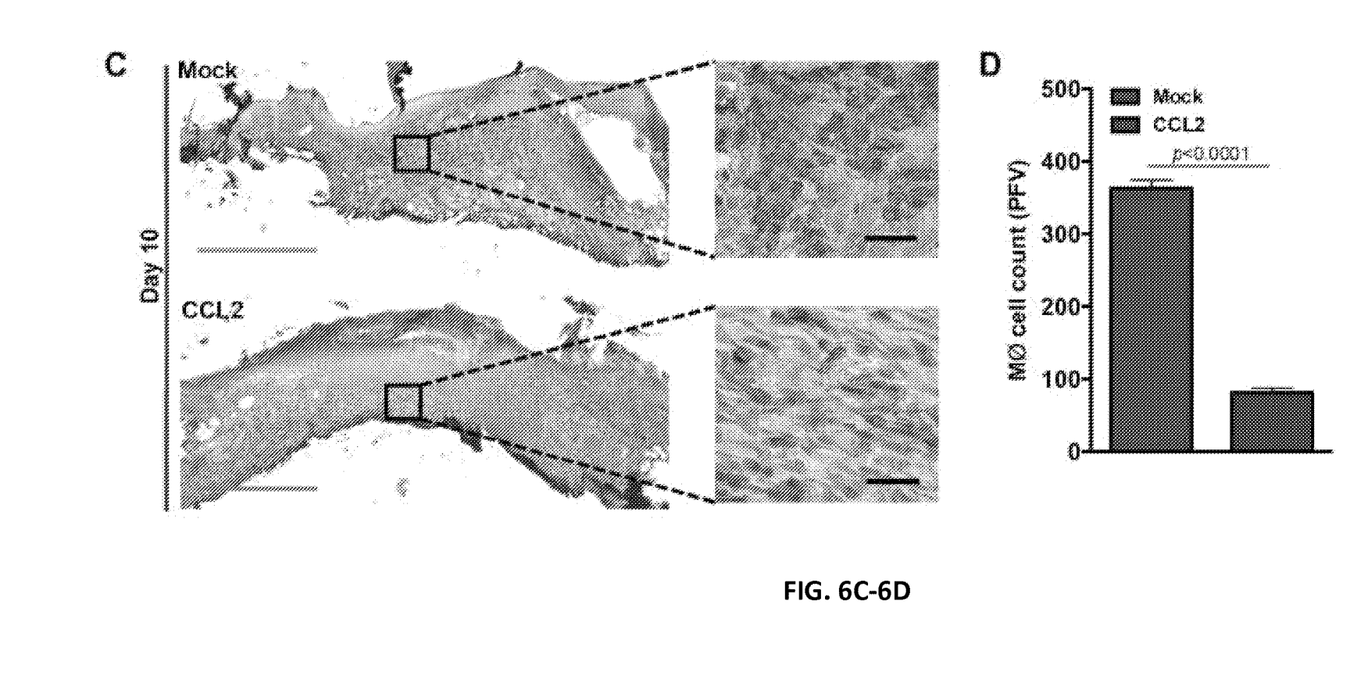
FIG. 6C is a photograph of a histological section stained by CD68 antibody from a day-10 wound from a diabetic mouse subjected to mock treatment or treated with CCL2.
FIG. 6D is a bar graph quantifying macrophages in studies similar to those depicted in FIG. 6C.
Figures 6E, 6F:
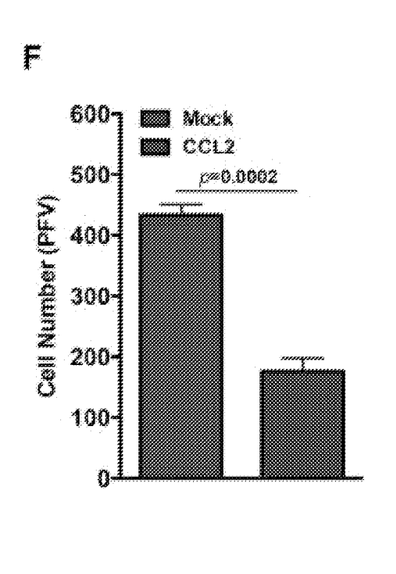
FIG. 6E is a photograph of a histological section stained by hematoxylin and eosin from a day-10 wound from a diabetic mouse subjected to mock treatment or treated with CCL2.
FIG. 6F is a bar graph quantifying macrophages in studies similar to those depicted in FIG. 6E.

CCL2 treatment enhances wound healing in diabetic wounds, as assessed by digital photography and wound area measurements (FIGS. 6A and 6B, p<0.0001, n=4). These results are further corroborated by histological analyses which indicate that in contrast to the mock-treated diabetic wounds that are only partially re-epithelialized by day 10, the CCL2-treated diabetic wounds were completely re-epithelialized, exhibit epidermal contraction and thickening with pronounced rete ridges, and enhanced granulation tissue (FIG. 6E). Inflammatory and macrophage responses are significantly reduced in the CCL2-treated day 10 wounds, as compared to the mock-treated wounds (FIGS. 6C-6F, p≤0.0001, n=4).

It has been reported that diabetic liver is more susceptible to *Listeria monocytogenes* infection. This phenomenon has been correlated with reduced CCL2 (MCP-1) expression in db/db liver, which suggests that inadequate macrophage response, due to CCL2 insufficiency, may be to blame for enhanced susceptibility to infection in that environment.

Further, reduced macrophage cell numbers have been observed in thioglycollate-induced inflammatory cells collected from the peritoneal cavity in db/db mice [11], indicating reduced macrophage infiltration in that environment.

Likewise, it has been reported that granulocytemacrophage colony-stimulating factor (GM-CSF) enhanced wound healing in diabetes by upregulating pro-inflammatory cytokines. Interestingly, CCL2 is one of the upregulated pro-inflammatory cytokines under these conditions.

Prolonged use of anti-inflammatory agents, has demonstrated deleterious impact on various aspects of wound healing, including an anti-proliferative effect, weakened breaking strength, reduced wound contraction, delayed reepithelialization, impaired angiogenesis, and reduced growth factor expression. An opposite approach, one that is based on pro-inflammatory chemokines, may be more appropriate to stimulate healing in diabetic wounds. CCL2 treatment can significantly enhance healing in diabetic wounds (FIG. 6) by restoring the macrophage response (FIG. 5). These data demonstrate that treatment with a pro-inflammatory cytokine in the early stages can have a dramatic yet positive impact on healing. Interestingly, CCL2-treated wounds do not remain inflamed and are able to resolve the inflammatory response by day 10 (FIGS. 6C-6F), indicating that diabetic tissues are not destined to become locked in the persistent and hyper-inflammatory mode, which is a factor contributing to impaired healing in diabetic chronic ulcer. These data suggest that the restoration of the proper kinetics of macrophage response may be able to jumpstart subsequent healing stages. Thus, CCL2 chemokine-based therapy may be an attractive strategy to promote healing in diabetic wounds.

The term "treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to wounds or a halting in the progression of the diabetic wounds.

The compounds such as cytokines may be used alone or in compositions together with a pharmaceutically acceptable carrier or excipient.

When the term "cytokines" is used, it is principally in reference to CCL2 alone or in combination with one or more cytokines, including MIP-1 alpha, MIP-1 beta, Rantes, KC, MIP-2, LIX, GM-CSF, CCL20, interleukin IL-1 beta phorbol myristate acetate (PMA); and the like.

Pharmaceutical compositions of the present invention comprise a therapeutically effective amount of a cytokine, particularly CCL2, formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The cytokines may be administered to diabetic wounds in humans (after debridement) and other animals topically in dosage unit formulations containing conventional nontoxic pharmaceutically acceptable carriers, adjuvants, and vehicles as desired. Topical administration may also involve the use of transdermal administration such as transdermal patches or ionophoresis devices.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, lyophilized powders, transdermal patches or other forms known in the art.

Among the acceptable vehicles and solvents that may be employed are water, Phosphate buffered saline (PBS), Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of an administered drug form may be accomplished by dissolving or suspending the drug in an oil vehicle.

Dosage forms for topical or transdermal administration of a compound of this invention include ointments, pastes, creams, lotions, gels, powders, solutions, sprays, or patches. The active component is admixed under sterile conditions with a pharmaceutically acceptable carrier and any needed preservatives or buffers as may be required.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

A cytokine can be administered alone or in combination with a other compounds intended to treat ulcer or wound healing or other compounds palliative to diabetic patients in particular, possible combination therapy taking the form of fixed combinations or the administration of a cytokine and other compound being staggered or given independently of one another. Long-term therapy is equally possible as is adjuvant therapy in the context of other treatment strategies, as described above. Effective amounts of the compounds of the invention generally include any amount sufficient to detectably improve healing of a wound in a diabetic patient, including those associated with chronic diabetic ulcer. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, drug combination, and the severity of the particular disease undergoing therapy. The therapeutically effective amount for a given situation can be readily determined by routine experimentation and is within the skill and judgment of the ordinary clinician.

According to the methods of treatment of the present invention, a wound in a diabetic patient such as a human or lower mammal by administering to the patient an amount of a cytokine such as CCL2, in such amounts and for such time as is necessary to achieve the desired result. An "amount that is effective to aid healing of a wound in a diabetic patient" of a cytokine refers to a sufficient amount of the cytokine alone or in combination with other compounds to treat diabetic wounds including those associated with chronic diabetic ulcer, at a reasonable benefit/risk ratio applicable to any medical treatment.

It will be understood, however, that the total daily usage of the compounds and compositions of the present invention will be decided by the attending physician within the scope of sound medical judgment. In some embodiments a single dose right after wound debridement initially to jumpstart the subsequent stages of healing may be administered. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration; the duration of the treatment; drugs used in combination or coincidental with the specific compound employed; and like factors well known in the medical arts.

While the present invention has been described in terms of preferred embodiments, it will be understood, of course, that the invention is not limited thereto since modifications may be made to those skilled in the art, particularly in light of the foregoing teachings.

The invention claimed is:

1. A method of treating a wound in a diabetic patient comprising administering a therapeutically effective amount of an isolated protein comprising Chemokine (C-C motif) ligand 2 (CCL2) to a wound site.

2. The method according to claim 1, wherein the diabetic patient has type II or adult-onset diabetes.

3. The method according to claim 1, comprising administering the therapeutically effective amount of CCL2 within about one day of appearance of the wound site.

4. The method according to claim 1, comprising debriding the wound site and administering the therapeutically effective amount of CCL2.

5. The method according to claim 1, wherein the patient suffers from a chronic diabetic ulcer.

6. The method according to claim 1, comprising administering the therapeutically effective amount of CCL2 when the wound site has a lower-than-expected amount of CCL2 relative to a normal subject as determined by a macrophage migration assay.

7. The method according to claim 1, comprising administering the therapeutically effective amount of CCL2 as a single dose.

8. The method according to claim 1, comprising topically administering the therapeutically effective amount of CCL2.

9. The method according to claim 1, comprising administering the therapeutically effective amount of the isolated protein comprising CCL2 and a second agent.

10. The method according to claim 9, wherein the second agent is selected from the group consisting of Macrophage Inflammatory Protein-1 alpha (MIP-1 alpha), Macrophage Inflammatory Protein-1 beta (MIP-1 beta), Regulated on Activation, Normal T Cell Expressed and Secreted (Rantes), keratinocyte-derived cytokine (KC), Macrophage Inflammatory Protein-2 (MIP-2), Lipopolysaccharide-induced CXC chemokine (LIX), Granulocyte-macrophage colony-stimulating factor (GM-CSF), Chemokine (C-C motif) ligand 20 (CCL20), interleukin IL-1 beta (IL-1 beta) and phorbol myristate acetate (PMA).

11. The method according to claim 1, comprising administering the therapeutically effective amount to the wound site in an amount sufficient to restore the macrophage response.

12. The method according to claim 1, wherein the therapeutically effective amount of CCL2 administered is about 10 ng to about 100 ng per wounded area of about 3 mm to about 5 mm.

13. The method according to claim 1, wherein the dose of CCL2 administered is about 20 ng to about 90 ng per wounded area of about 3 millimeters to about 5 millimeters.

14. The method according to claim 1, wherein the dose of CCL2 administered is about 30 ng to about 80 ng per wounded area of about 3 millimeters to about 5 millimeters.

15. The method according to claim 1, wherein the dose of CCL2 administered is about 50 ng to about 75 ng per wounded area of about 3 millimeters to about 5 millimeters.

16. The method according to claim 1, wherein the dose of CCL2 administered is about 60 ng per wounded area of about 3 millimeters to about 5 millimeters.

* * * * *